United States Patent [19]

Brenman et al.

[11] Patent Number: 4,765,343

[45] Date of Patent: Aug. 23, 1988

[54] APPARATUS FOR TRANSFERRING ELECTRICAL ENERGY TO AND FROM LIVING TISSUE

[75] Inventors: Henry S. Brenman, Cinnaminson; Benjamin Jarmolow, Cherry Hill, both of N.J.

[73] Assignee: Biosonics, Inc., Philadelphia, Pa.

[21] Appl. No.: 696,048

[22] Filed: Jan. 29, 1985

[51] Int. Cl.⁴ .............................................. A61B 5/04
[52] U.S. Cl. .................................. 128/639; 128/381; 128/800
[58] Field of Search ............... 128/381, 639, 644, 783, 128/796, 798, 800

[56] References Cited

U.S. PATENT DOCUMENTS

| | | | |
|---|---|---|---|
| 206,474 | 7/1878 | Morel | 128/800 |
| 500,767 | 7/1893 | Hetherington-Carruthers | 128/798 |
| 1,545,413 | 7/1925 | Elmvall | 128/800 |
| 3,845,771 | 11/1974 | Vise | 128/800 |
| 4,510,939 | 4/1985 | Brenman et al. | 128/639 |

Primary Examiner—Lee S. Cohen
Assistant Examiner—Randy Citrin
Attorney, Agent, or Firm—Robert C. Podwil

[57] ABSTRACT

Apparatus for transferring electrical energy to and from living tissue comprises a glove of thin, flexible elastomeric material, which carries electrodes, electrically connected to a connector disposed at the cuff of the glove. The connector permits the electrodes to be electrically connected to a source of electrical energy or to a load, so that electrical energy may be applied to or drawn from living tissue.

17 Claims, 3 Drawing Sheets

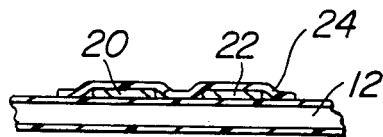
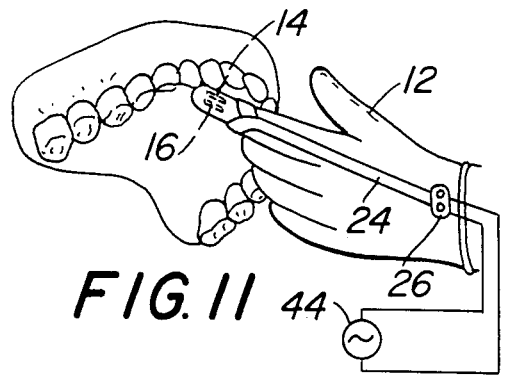
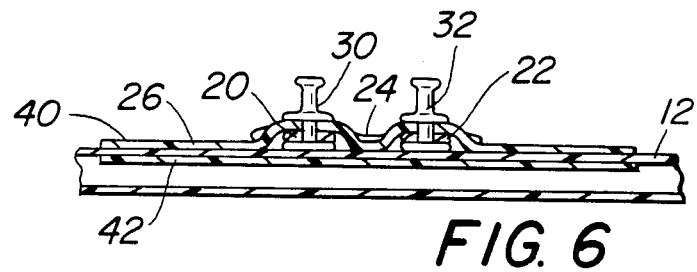
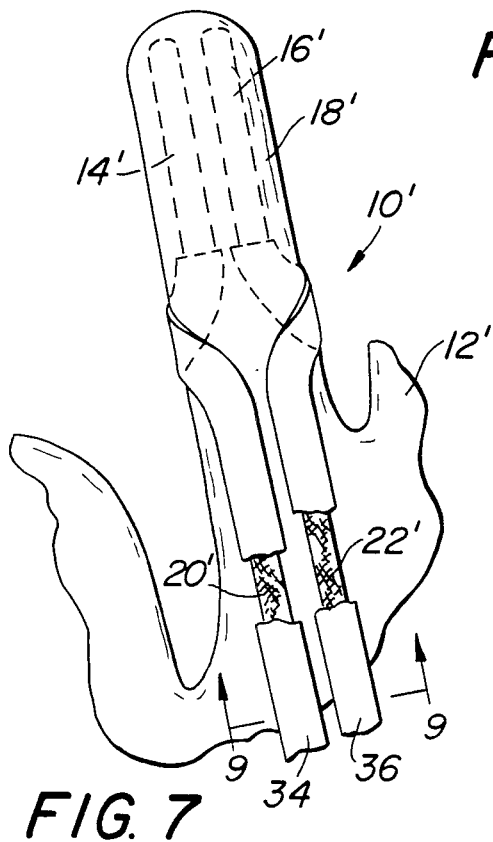
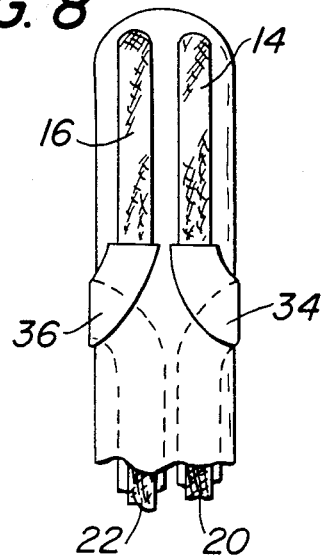
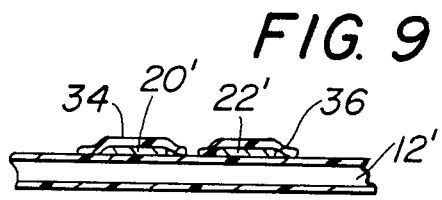

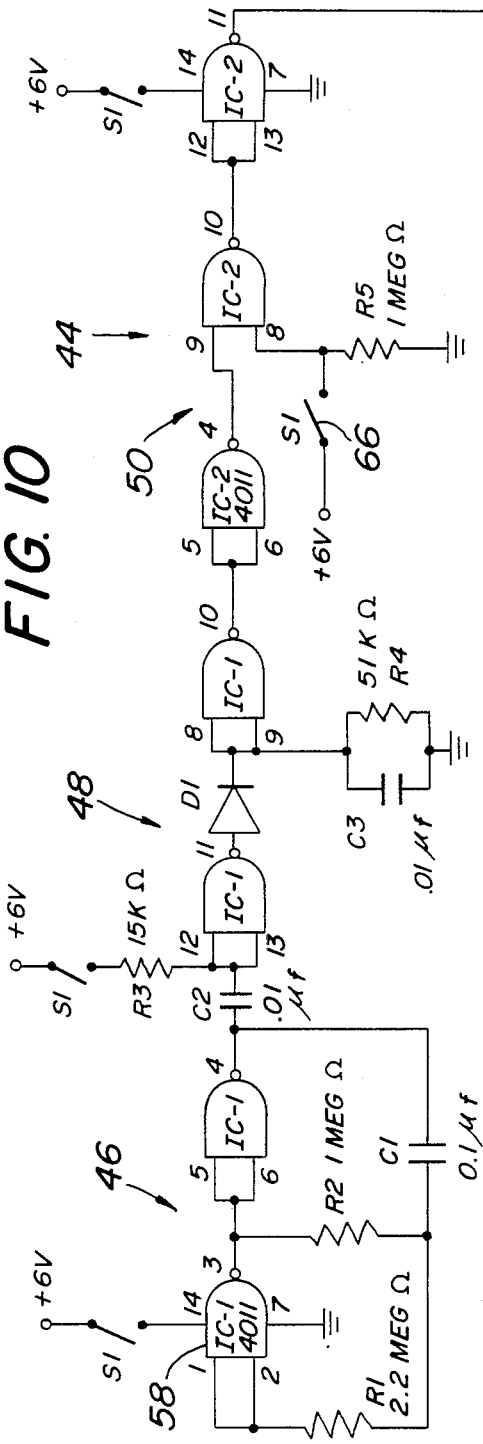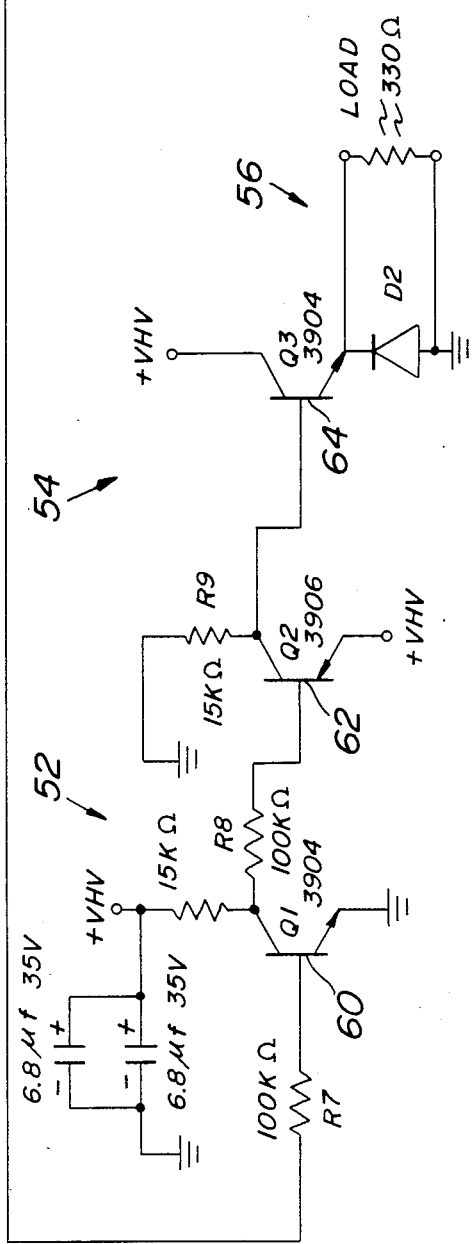
FIG. 10

APPARATUS FOR TRANSFERRING ELECTRICAL ENERGY TO AND FROM LIVING TISSUE

BACKGROUND OF THE INVENTION

This invention relates to apparatus for applying electrical stimuli to living tissue, or for transferring electrical energy from living tissue, for diagnostic purposes. In addition, the invention relates to apparatus for transferring electrical energy from living tissue to measuring, display and recording equipment used in operating rooms or physicians' offices.

In certain medical procedures, it is useful or desirable to apply electrical energy to tissues of the body. For example, in connection with copending U.S. patent application Ser. No. 452,119, filed Dec. 22, 1982, now U.S. Pat. No. 4,542,753 "Apparatus And Method For Stimulating Penile Erectile Tissue", assigned to the assignee of the present application, the suitability of a particular candidate for use of the apparatus disclosed therein may be determined by palpating the prostate gland, and applying electrical energy to that gland so as to simulate the action of the apparatus. Similarly, the locations of critical regions or spots on the prostate gland can be determined by applying electrical energy to the prostate gland from a signal generator via the apparatus to the living tissue. The regions or spots at which a desired reaction, in that instance incipient erection, is stimulated, can thus be identified. Further, in connection with the above application, topical application of electrical energy to the anal area is desirable to induce contraction of the musculature of the rectum as an aid to intimately fitting a device to the rectal cavity.

Certain other diagnostic procedures involve the transference of electrical energy from tissues to recording devices. In cardiology, for example, in cardiac mapping, low voltages produced by the heart are sensed and transferred to recording or display devices.

Co-pending U.S. patent application Ser. No. 452 319, filed Dec. 22, 1982, now U.S. Pat. No. 4,510,939 for "Means For Transferring Electrical Energy To And From Living Tissue", assigned to the assignee of the present application, discloses apparatus for the present purpose, in which individual electrodes are affixed to fingers and the thumb of a glove of flexible fluid impervious elastomeric material. With such apparatus, the glove may be used for digital palpation, and the electrodes precisely positioned with respect to palpated spots. The present invention is an improved and more effective apparatus of the same general type, but in which the electrodes are more advantageously and efficaciously placed, and in which the conjunction of the thumb and a finger is not essential to operation.

Other advantages of the present apparatus will appear hereinafter.

The objects of the present invention are realized, in a presently preferred form of the apparatus, by mounting on a glove of natural or synthetic rubber or rubber-like elastomeric material, electrodes for applying energy to the tissues or for receiving energy from them. Also mounted on the glove, and preferably integrally formed with the electrodes, are electrical conductors connecting the electrodes to an electrical connector, which serves to couple the apparatus to a source of electrical energy or to amplifying or display devices. The source of electrical energy may be a signal generating circuit or simply a source of electrical potential, as the application may require. The electrodes and associated conductors are, in the presently preferred form of the apparatus, applied to a single finger of the glove, and are flexible so as not to impede the normal flexibility of the glove or to render the glove less useful for normal palpation than conventional surgical gloves. The electrodes are spaced from each other in such a fashion that the application of finger pressure during palpation places the electrodes in intimate contact with the palpated tissues, and establishes a circuit between the electrodes, through the palpated tissues.

There are seen in the drawings forms of the invention which are presently preferred (and which present the best mode contemplated for carrying the invention into effect), but it should be understood that the invention is not limited to the precise arrangements and instrumentalities shown.

DESCRIPTION OF THE DRAWINGS

FIG. 5 is a partial cross-sectional view taken along the line 5—5 in FIG. 1.

FIG. 6 is a partial cross-sectional view, taken along the line 6—6 in FIG. 1.

FIG. 7 is a partial view, showing part of the palmar surface of another embodiment of a glove in apparatus in accordance with the invention.

FIG. 8 is a partial view, similar to FIG. 2, but showing the embodiment of FIG. 7.

FIG. 9 is a partial cross-sectional view, taken along the line 9—9 in FIG. 7.

FIG. 10 is a schematic diagram, illustrating exemplary electronic circuit means, which may be used to generate a signal for use with the invention.

FIG. 11 illustrates the manner in which the invention may be used to locate desired areas and to transfer electrical energy to or from those areas.

DETAILED DESCRIPTION

Figures 1, 2, 3, 4:
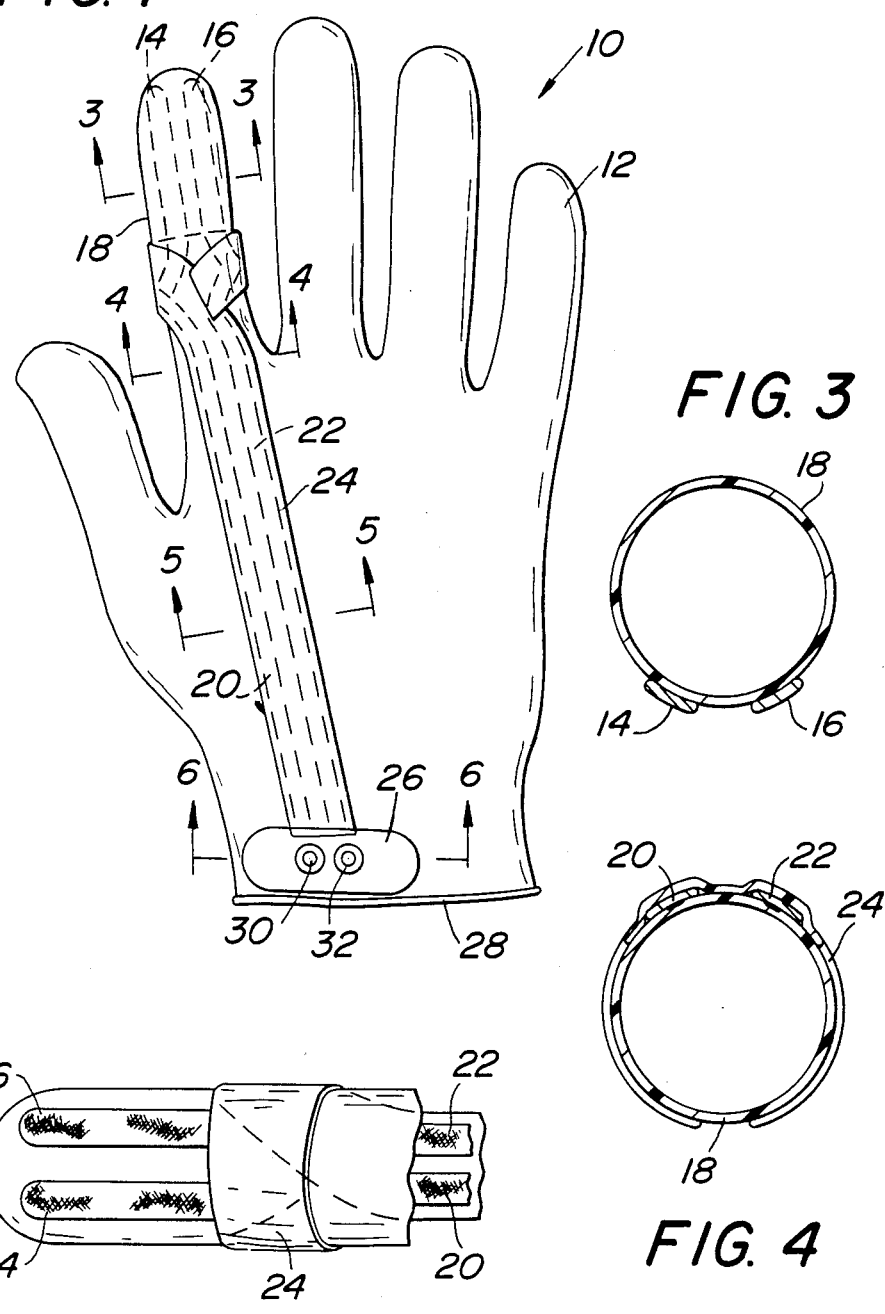
FIG. 1 is a plan view of the dorsal aspect of a glove incorporating the principles of the present invention.
FIG. 2 is a partial view, showing the palmar surface of a finger of a glove of the kind seen in FIG. 1.
FIG. 3 is a cross-sectional view, taken along the line 3—3 in FIG. 1.
FIG. 4 is a cross-sectional view, taken along the line 4—4 in FIG. 1.

Referring now to the drawings in detail, wherein like reference numerals indicate like elements, there is seen in FIG. 1 apparatus designated generally by the reference numeral 10.

The apparatus 10 includes a glove 12, of natural or synthetic rubber or rubber-like elastomeric material. The glove 12, but for the special features to be described below, may be a conventional surgical glove of the well-known and readily available kind. Such gloves are "thin," in the sense that they are so designed as to allow for a sensitive "feel" through their material, and highly flexible so as not to impede to any significant degree the manual dexterity of a wearer. Affixed to the glove 12 are a plurality of planar electrodes whose shape may conform to that of a user's finger. As is seen in FIGS. 1 and 2, for example, electrodes 14 and 16 are spaced from each other and disposed approximately beneath the distal phalange of the index finger 18 of the glove 12. The electrodes 14 and 16 preferably extend distally from the joint between the middle and distal phalanges of the finger, and lie in a generally parallel spaced relationship. Although the electrodes 14 and 16 are illustrated in association with an index finger, they could, consistently with the principles of the invention, be associated with another finger of the glove 12.

Referring again to FIG. 1, it will be seen that the electrodes 14 and 16 are extensions of conductors 20 and 22, the conductor 20 is being associated with the electrode 14, and the conductor 22 being associated with the electrode 16.

As is apparent from FIGS. 1 and 2, the electrodes 14 and 16 and conductors 20 and 22 are affixed to the external surface of the glove 12. In a presently preferred form of the invention, the electrodes 14 and 16 and conductors 20 and 22 are strips of electrically conductive material, such as, for example, the commercially available woven textile cloth sold by Swift Textile Metalizing Corp., of Hartfield, Conn. Such cloth includes silver threads, which provide the desired conductivity. The cloth is also soft, flexible, palpable and stretchable in all directions. Such cloth, moreover, characteristically distributes stimulation energy over the entire area of contact of the electrodes 14 and 16 with the tissues of a subject, thus tending to avoid inducing pain, which is sometimes associated with unduly concentrated applications of energy to a local area of the anatomy.

Referring again to FIGS. 1 and 2, an insulating overlayer such as an insulating strip 24 is applied over the conductors 20 and 22 to limit electrical contact with the subject to the areas of the electrodes 14 and 16. In the embodiment shown in FIGS. 1 and 2, the insulating strip 24 overlies both of the conductors 20 and 22, and is wrapped around the finger 18 at approximately the joint between the middle and distal phalanges.

Referring again to FIG. 1, the conductors 20 and 22 traverse the dorsal surface of the glove 12, wrapping around lateral surfaces of the finger 18 and extending from the respective electrodes 14 and 16 to respective halves of a multiple pin type connector 26, secured adjacent to the cuff 28 of the glove 12. The connector 26 typically comprises snap or frictionally inter-engageable parts 30 and 32, provided, respectively, with male and female (not shown) elements. Other suitable connectors may be used. The elements may be so connected to the electrodes as to render selected electrodes functional in a given situation. For example, for certain palpation procedures and applications, such as the diagnostic technique set forth in the above-identified co-pending application, it may be desirable to use the electrode 14 as an active or stimulating electrode, and the electrode 16 as "return" or ground electrode. In such a situation, it is feasible to apply stimulating voltage to the part 30 of the connector 26, and to connect the part 32 to a return or ground wire.

Referring now to FIGS. 7, 8 and 9 there is seen an alternative form 10' of the apparatus 10, in which elements corresponding to those previously described are designated by like primed (') reference numerals. The apparatus 10' illustrated in FIGS. 7, 8 and 9 employs, as an alternative to the above - described insulating strip 24, a pair of insulating strips 34 and 36, associated, respectively, with the conductors 20' and 22'. The insulating strips 34 and 36 provide an insulating overlayer, and like the strip 24, limit electrical contact with the subject to the areas of the electrodes 14' and 16'. The insulating strips 34 and 36 follow the course of the conductors 20' and 26', and wrap around lateral surfaces of the finger 18' to the palmar surface of the finger 18'.

The insulating strips 24, 34 and 36 must be of a material, and of such a thickness that they do not interfere with the stretchability of the glove 12, and they must return to their original size after stretching with substantially the same degree of resilience as the material of the glove. Puckering of the glove, as would occur if the strips 24, 34 and 36 interferred with stretchability of the glove 12, can render the glove unsuitable for its intended use.

FIG. 11 illustrates, somewhat diagrammatically, the manner in which the present invention may be used to transfer electrical energy to living tissue, in this instance, an area of the palate. In FIG. 11, the electrodes 14 and 16 on the glove 12 are shown in contact with the palate, as they would be in evaluating a potential candidate for use of the device described in U.S. patent application Ser. No. 481,331, filed Apr. 1, 1983, for "Apparatus and Method for Stimulating Salivation", assigned to the assignee of the present application.

The manner in which the glove 12 may be made will occur to those skilled in the art, and numerous fabrication techniques are possible. In one presently contemplated technique, the conductive cloth which provides the electrodes 14, 16 and conductors 20, 22, after having been cut to desired dimensions, is affixed to the glove 12, using rubber adhesive applied to the forefinger of the glove 12 in the area of electrodes 14 and 16 and at locations spaced by perhaps 2.5 cm. along the course of the conductors 20, 22. The snap-engageable parts 30 and 32 of the connector 26, together with a reinforcing patch 40 of surgical tape or the like, may be affixed to the ends of the conductors 20 and 22, and then applied to the glove 12. Another reinforcing patch 42 may be provided on the reverse (in-side) of the glove in juxtaposition to the patch 40. Next, the insulating strip 24 or, as the case may be, insulating strips 34 and 36, may be applied. The insulating strips 24, 34, 36 may be made from pressure sensitive latex patches or other commercially available materials.

The particular dimensions of the electrodes 14 and 16 and the conductors 20 and 22, and of the spacing between the electrodes 14 and 16, may vary from one operative embodiment to another. In one presently preferred embodiment, however, the electrodes 14 and 16 (and the conductors 20 and 22), have widths of one cm. (0.394 in.) and the electrodes 14 and 16 are spaced apart by 0.75 cm. (0.295 in.). With the voltages and frequencies involved in stimulation, such dimensions and spacing have been found to provide satisfactory electrical performance, without undue discomfort to the subject.

FIG. 10 illustrates an example of an electronic circuit by which a stimulating signal can be produced for use in association with a glove 12 for diagnostic purposes, although numerous other specific sources of potential or signal generators may be used with the apparatus 10. The circuit of FIG. 10, it should be understood, is not per se, a part of the present invention.

The illustrated circuitry, designated generally by the reference numeral 44, includes an astable multivibrator, designated generally by the reference numeral 46; a monostable multivibrator, designated generally by the reference numeral 48; NAND gating 50; a pair of inverters 52 and 54; and an emitter-follower 56 providing a stimulating voltage output.

A power supply, not shown, may provide the signal generator circuitry 44 with logic level voltage (approximately 6v. D.C.) and stimulating level voltage (approximately 24 v. D.C.) inputs, the logic level voltage inputs serving to power the circuitry 44 and the stimulating level voltage inputs providing the signal to be applied to the electrodes.

The astable multivibrator 46 and monostable multivibrator 48, which comprise the first and second stages of the circuitry 44, provide pulses of logic level voltage and of a desired pulse-width and frequency. In the illustrated circuitry 44, the astable multivibrator 46 produces a series of square pulses at an amplitude of about 6 volts and a frequency of about 30 to 33 Hz, and the monostable multiviorator 46 serves to shape the pulses to a width of 500 microseconds. The principal components of the illustrated astable and monostable multivibrators 46, 48 are commercially available integrated circuits. The integrated circuit 58, for example, and the other integrated circuits labeled "IC-1" and "IC-2," may be CMOS No. 4011 integrated circuits available from numerous manufacturers, including, among others, RCA, Texas Instrument Corp., National Semiconductor, and Solid State Scientific. All of the other components in the illustrated circuitry 44 are also commercially available items. The transistor 60 used in the inverter circuit 52 may be of the 2N 3904 type. The transistor 62 in the inverter circuit 54 may be of the 2N 3906 type. The transistor 64 may also be of the 2N 3906 type.

Operation of the switch 66 applies to the astable multivibrator 46, monostable multivibrator 48, and other aspects of the circuitry 44, the logic voltage supply. An output pulse will be repetitively supplied during the time in which the circuitry 44 is so powered. In other words, output is enabled by closing of the switch 66, and inhibited when the switch 66 is open.

The output of the circuitry illustrated in FIG. 10 may be applied to the connector 26, and through the connector 26 to the electrodes 14 and 16. The switch 66 enables the glove 12 to be used for palpation or to be otherwise positioned with assurance that the circuitry 44 is inhibited, thus eliminating undesirable effects such as untimely or unwanted stimulation affecting extraneous tissues. It will be understood that when the output pulse is inhibited, the output is zero volts. When the output is enabled, the actual output level is a function of the voltage of the stimulating voltage supply. In one operative embodiment of the circuitry 44, the stimulating voltage supply provides about twenty-four volts, and the output is within 0.5 volts of this voltage and substantially constant for 500 microseconds when driving a 330 ohm load.

The present invention may be embodied in other specific forms without departing from its spirit and essential attributes and, accordingly, reference should be made to the appended claims rather than the foregoing specification as indicating the scope of the invention.

We claim:

1. Apparatus for selectively transferring electrical energy to and from critical localities in living tissue for diagnostic purposes, comprising a glove of flexible fluid impervious elastomeric material, said material being sufficiently thin and flexible to afford to the wearer substantially unimpeded feel and manual dexterity so as to enable use of said glove for digital palpation while transferring energy to and from tissue, and a pair of electrodes, said electrodes comprising flexible layers of electrically conductive material affixed to the surface of a finger of said glove, said electrodes being spaced from each other and electrically unconnected to each other, and disposed at areas of the glove adapted to be beneath the distal portion of the finger of a wearer of said glove, thereby to facilitate simultaneous application of said electrodes by digital direction and pressure to a palpated locality of tissue, an electrical connector coupled to said glove and adapted to be electrically connected to electrical circuitry external to said glove, and a plurality of flexible electrical conductors coupled to said glove and electrically connecting said electrodes and said connector.

2. Apparatus in accordance with claim 1, wherein said conductors comprise flexible layers of electrically conductive material affixed to the surface of said glove.

3. Apparatus in accordance with claim 2, wherein said electrodes cover areas adapted to be beneath at least approximately the palmar surface of the distal phalange of the finger of a wearer of said glove.

4. Apparatus in accordance with claim 3, wherein said electrodes comprise electrically conductive strips, elongated in an axial direction with respect to said finger of said glove to which they are affixed and generally parallel to each other.

5. Apparatus in accordance with claim 4, wherein said electrodes are disposed, when said glove is worn, on areas of the glove adapted to be on opposite sides of a sagittal plane of the finger of the user.

6. Apparatus in accordance with claim 5, wherein said electrodes are disposed on the index finger of said glove.

7. Apparatus in accordance with claim 6, wherein said flexible layers comprise woven textile cloth having electrically conductive threads therein, said electrodes and said conductors comprising strips of said cloth.

8. Apparatus in accordance with claim 1, wherein said electrodes are disposed on the index finger of said glove and cover areas adapted to be beneath at least approximately the distal phalanges of the index finger of a wearer of said glove, said electrodes comprising electrically conductive strips, elongated in an axial direction with respect to the index finger of said glove.

9. Apparatus in accordance with claim 8, wherein said electrodes are generally parallel to each other and disposed, when said glove is worn, on areas of the glove adapted to be on opposite sides of a sagittal plane of the index finger of the user.

10. Apparatus in accordance with claim 9, wherein said electrodes and said conductors comprise flexible layers of electrically conductive material affixed to the surface of said glove, said electrodes and said conductors comprising strips of said material.

11. Apparatus in accordance with claim 10, wherein said flexible layers comprise woven textile cloth having electrically conductive threads therein.

12. Apparatus in accordance with claim 11, wherein said conductors traverse the dorsal surface of said glove and are wrapped around lateral surfaces of said index finger of said glove to the palmer surface of said index finger.

13. Apparatus in accordance with claim 12, wherein said electrical connector is coupled to said glove adjacent to the cuff of said glove.

14. Apparatus in accordance with claim 13, and insulating means overlying said conductors from said electrodes to said electrical connector.

15. Apparatus in accordance with claim 14, wherein said insulating means comprises a single strip of insulating material overlying said conductors.

16. Apparatus in accordance with claim 14, wherein said insulating means comprises respective strips of insulating material overlying respective conductors.

17. Apparatus for selectively transferring electrical energy to and from critical localities in living tissue for diagnostic purposes, comprising a glove of flexible fluid impervious elastomeric material, said material being sufficiently thin and flexible to afford to the wearer substantially unimpeded feel and manual dexterity so as to enable use of said glove for digital palpation which transferring energy to and from tissue, and a plurality of electrodes, said electrodes comprising flexible layers of electrically conductive material affixed to the surface of a finger of said glove, said electrodes being spaced from each other and electrically unconnected to each other and disposed at areas of the glove adapted to be beneath the distal portion of the finger of a wearer of said glove, thereby to facilitate simultaneous application of said electrodes to a palpated locality of tissue, an electrical connector coupled to said glove and adapted to be electrically connected to electrical circuitry external to said glove, and a plurality of flexible electrical conductors coupled to said glove and electrically connecting said electrodes and said connector.

* * * * *

UNITED STATES PATENT AND TRADEMARK OFFICE
CERTIFICATE OF CORRECTION

PATENT NO. : 4,765,343
DATED : August 23, 1988
INVENTOR(S) : Henry S. Brenman & Benjamin Jarmolow It is certified that error appears in the above-identified patent and that said Letters Patent are hereby corrected as shown below:

In claim 1, line 14, delete the word "portion" and insert the word --phalange--.

In claim 17, line 14, delete the word "portion" and insert the word --phalange--.

Signed and Sealed this

Twenty-eighth Day of February, 1989

Attest:

DONALD J. QUIGG

Attesting Officer

Commissioner of Patents and Trademarks